United States Patent
White et al.

(10) Patent No.: US 9,380,979 B2
(45) Date of Patent: Jul. 5, 2016

(54) APPARATUS AND METHOD OF ASSEMBLING AN APPARATUS FOR SENSING PRESSURE

(71) Applicant: Nokia Corporation, Espoo (FI)

(72) Inventors: Richard White, Huntingdon (GB); Chris Bower, Cambridgeshire (GB)

(73) Assignee: Nokia Technologies Oy, Espoo (FI)

( * ) Notice: Subject to any disclaimer, the term of this patent is extended or adjusted under 35 U.S.C. 154(b) by 196 days.

(21) Appl. No.: 13/667,457

(22) Filed: Nov. 2, 2012

(65) Prior Publication Data

US 2014/0128687 A1    May 8, 2014

(51) Int. Cl.
| | |
|---|---|
| H01G 5/18 | (2006.01) |
| H01G 5/16 | (2006.01) |
| H01G 5/011 | (2006.01) |
| H01G 5/013 | (2006.01) |
| A61B 5/00 | (2006.01) |
| G01R 27/26 | (2006.01) |
| H01R 43/16 | (2006.01) |
| A61B 5/021 | (2006.01) |

(52) U.S. Cl.
CPC ............ *A61B 5/6801* (2013.01); *A61B 5/02141* (2013.01); *G01R 27/2605* (2013.01); *H01G 5/011* (2013.01); *H01G 5/013* (2013.01); *H01G 5/16* (2013.01); *H01R 43/16* (2013.01); *A61B 2562/0214* (2013.01); *A61B 2562/0247* (2013.01); *A61B 2562/0285* (2013.01); *Y10T 29/49204* (2015.01)

(58) Field of Classification Search
CPC ............. H01G 4/30; H01G 5/18; H01G 5/16; H01G 5/011; H01G 5/013
USPC ......................................................... 361/277
See application file for complete search history.

(56) References Cited

U.S. PATENT DOCUMENTS

| | | | |
|---|---|---|---|
| 7,208,960 B1 | 4/2007 | Deangelis et al. | ............ 324/661 |
| 2007/0229464 A1 | 10/2007 | Hotelling et al. | |
| 2008/0316678 A1 | 12/2008 | Ehrenberg et al. | ............ 361/503 |
| 2009/0001045 A1 | 1/2009 | Chen et al. | |
| 2009/0103236 A1* | 4/2009 | Nonaka | ................. C03C 17/007 361/320 |

(Continued)

FOREIGN PATENT DOCUMENTS

| | | |
|---|---|---|
| CN | 1388364 A | 1/2003 |
| CN | 101034702 A | 9/2007 |

(Continued)

OTHER PUBLICATIONS

Hu, W., et al.; *Elastomeric transparent capacitive sensors based on an interpenetrating composite of silver nanowires and polyurethane*, Appl. Phys. Lett. 2013, vol. 102, pp. 083303-1-083303-5.

(Continued)

*Primary Examiner* — Eric Thomas
*Assistant Examiner* — Arun Ramaswamy
(74) *Attorney, Agent, or Firm* — Harrington & Smith

(57) ABSTRACT

An apparatus and method of forming an apparatus wherein the apparatus includes a first electrode and a second electrode arranged to form a parallel plate capacitor; a compressible, transparent dielectric layer provided between the first electrode and the second electrode wherein the dielectric layer has a nanostructure and the dimensions of the nanostructure are such that the dielectric layer is optically transparent.

20 Claims, 6 Drawing Sheets

(56) References Cited

U.S. PATENT DOCUMENTS

| | | | |
|---|---|---|---|
| 2009/0208842 A1 | 8/2009 | Harada et al. | 429/209 |
| 2009/0273483 A1 | 11/2009 | Tompkins et al. | 340/657 |
| 2009/0311484 A1* | 12/2009 | McLellan | B82Y 10/00 428/172 |
| 2010/0079926 A1* | 4/2010 | Tan | H01G 4/06 361/311 |
| 2010/0328845 A1 | 12/2010 | Hiralal et al. | 361/502 |
| 2011/0003069 A1 | 1/2011 | Ho et al. | 427/58 |

FOREIGN PATENT DOCUMENTS

| | | |
|---|---|---|
| CN | 101228646 A | 7/2008 |
| CN | 101258560 A | 9/2008 |
| CN | 101714453 A | 5/2010 |
| EP | 0756162 A2 | 10/2001 |
| EP | 2154503 A2 | 2/2010 |
| JP | 2007272898 A | 10/2007 |
| JP | 2007315875 A | 12/2007 |
| JP | 2009010375 A | 1/2009 |
| JP | 2009297837 A | 12/2009 |
| KR | 101148338 B1 | 5/2012 |
| KR | 20120122269 A | 11/2012 |
| WO | WO2006110162 A2 | 10/2006 |
| WO | WO2011114100 A1 | 9/2011 |
| WO | WO-2011155078 A1 | 12/2011 |

OTHER PUBLICATIONS

Mannsfeld, S.C.B., et al., "Highly sensitive flexible pressure sensors with microstructured rubber dielectric layers" © 2010 Macmillan Publishers Ltd., 6 pgs.

* cited by examiner

APPARATUS AND METHOD OF ASSEMBLING AN APPARATUS FOR SENSING PRESSURE

TECHNOLOGICAL FIELD

Embodiments of the present invention relate to an apparatus and method of assembling an apparatus for sensing pressure. In particular, they relate to an apparatus and method of assembling an apparatus for sensing pressure which may be used to measure physiological parameters of a user.

BACKGROUND

Sensors which may be worn on the body to measure parameters such as heart rate, galvanic skin response, temperature, pressure and acceleration are known. The outputs from such sensors may then be used to monitor the physiological condition of the user for example, during a period of activity or exercise or to assess the user for health purposes.

It may be beneficial to provide improved sensors to make them easier for a user to use and which may provide more accurate data.

BRIEF SUMMARY

According to various, but not necessarily all, examples of the disclosure, there may be provided an apparatus comprising: a first electrode and a second electrode arranged to form a parallel plate capacitor; a compressible, transparent dielectric layer provided between the first electrode and the second electrode wherein the dielectric layer has a nanostructure and the dimensions of the nanostructure are such that the dielectric layer is optically transparent.

In some examples the dielectric layer may be porous.

In some examples the dielectric layer may be formed from a block copolymer.

In some examples the nanostructure of the dielectric layer may be formed by self assembly of the block copolymer. The nanostructure of the dielectric layer may be formed by phase separation of the block copolymer. The dimensions of the nanostructure may be such that the nanostructure does not cause scattering of incident light.

In some examples the dimensions of the nanostructure may be less than 100 nm.

In some examples the first electrode may be formed on a curved surface. In some examples the electrodes may be transparent. In some examples the electrodes may be flexible.

In some examples the signal from the capacitor may be configured to be provided to measurement apparatus.

In some examples the apparatus is configured to be worn on a body of a user.

In some examples there may be provided an array comprising a plurality of apparatus as described in any of the preceding paragraphs.

According to various, but not necessarily all, examples of the disclosure, there may be provided a method comprising: forming a first electrode; forming a compressible, transparent dielectric layer overlaying the first electrode wherein the dielectric layer has a nanostructure and the dimensions of the nanostructure are such that the dielectric layer is optically transparent; forming a second electrode overlaying the dielectric layer to provide a parallel plate capacitor.

In some examples the first electrode may be formed by evaporating a conductive material onto a substrate. In some examples the substrate may be flexible.

In some examples the dielectric layer may be porous.

In some examples the dielectric layer may be formed from a block copolymer.

In some examples the nanostructure of the dielectric layer may be formed by self assembly of the block copolymer. In some examples the nanostructure of the dielectric layer may be formed by phase separation of the block copolymer.

In some examples the block copolymer solution may be coated overlaying the first electrode.

In some examples the second electrode may be adhered to the dielectric layer.

The apparatus may be for sensing pressure.

BRIEF DESCRIPTION

For a better understanding of various examples that are useful for understanding the brief description, reference will now be made by way of example only to the accompanying drawings in which.

DETAILED DESCRIPTION

The Figures illustrate an apparatus 1 comprising: a first electrode 3 and a second electrode 5 arranged to form a parallel plate capacitor; a compressible, transparent dielectric layer 7 provided between the first electrode 3 and the second electrode 5 wherein the dielectric layer 7 has a nanostructure and the dimensions of the nanostructure are such that the dielectric layer 7 is optically transparent.

Figure 1:
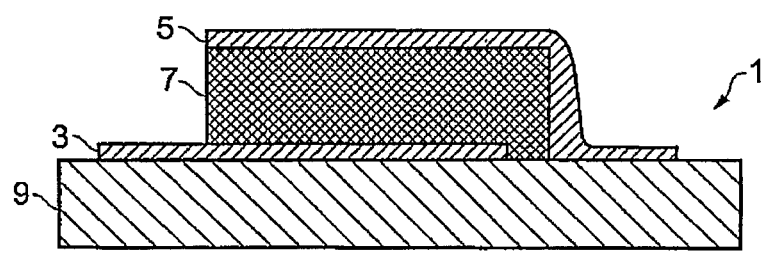
FIGS. 1A and 1B illustrate apparatuses according to examples of the disclosure.

FIG. 1 illustrates an example apparatus 1. The example apparatus 1 comprises a first electrode 3, a second electrode 5 and a dielectric layer 7. It is to be appreciated that only components of the apparatus 1 necessary for the following description are illustrated in FIG. 1 and that other components may be provided in other examples.

Figure 1B:
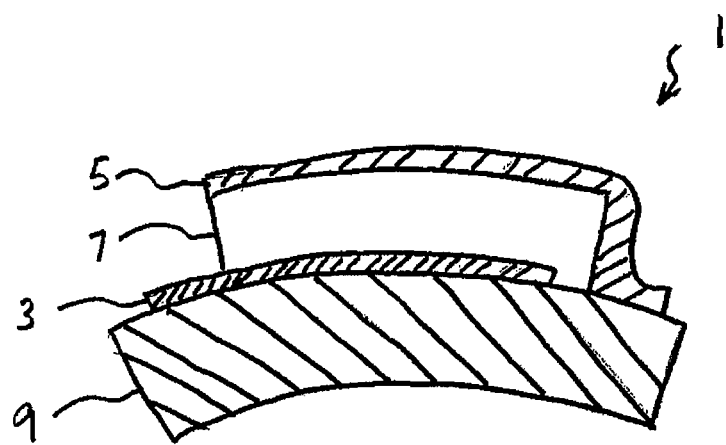

In the example of FIG. 1A the first electrode 3 is provided on the surface of a substrate 9. In the example illustrated in FIG. 1A the substrate 9 is flat. In other examples the substrate 9 may be curved, as illustrated in FIG. 1B.

In some examples the substrate 9 may be flexible or stretchable. The substrate 9 may be flexible or stretchable so that the apparatus 1 may be bent or deformed in response to a force applied by a user of the apparatus 1. The substrate 9 may be flexible or stretchable so as to enable the apparatus 1 to be comfortably and/or securely attached to the body of a user.

In some examples the substrate 9 may be transparent. The substrate 9 may be optically transparent so that visible light can pass through the apparatus 1. This may make the apparatus 1 suitable for use in, for example, display devices.

The substrate 9 may be made of any suitable material. In some examples the substrate 9 may be made of an electrically insulating material. In some other examples the substrate 9 may be made of a conductive or semiconductive material. In such examples the conductive or semiconductive material may be coated with an insulating material in order to not short the electrodes 3, 5. In some examples the substrate 9 may be semiconductive where the semiconductor is in the depletion regime so that no appreciable current flows within the substrate 9.

For example the substrate 9 may be made of a polymer such as polyethylene 2,6-naphthalate (PEN), polyethylene terephthalate (PET), polyimide (PI), polycarbonate (PC), polyethylene (PE), polyurethane (PU), polymethylmethacryclate (PMMA), polystyrene (PS). In examples the substrate 9 may comprise natural rubbers such as polyisoprenes, polybutadienes, polychloraprenes, polyisobutylenes, nitrile butadienes and styrene butadienes. In some examples the substrate 9 may comprise saturated elastomeric materials such as, polydimethylsiloxane (PDMS), Silicone rubbers, fluorosilicone rubbers, fluoroelastomers, perfluoroelastomers, ethylene vinyl acetate (EVA) thermoplastic elastomers such as styrene block copolymers, thermoplastic polyolefins, thermoplastic vulcanisates, thermoplastic polyurethane (TPU) thermoplastic copolyesters, melt processable rubbers or any other suitable material.

The first electrode 3 may comprise any suitable conductive material mounted on the substrate 9.

In some examples the first electrode 3 may also be flexible. The first electrode 3 may be flexible so that the apparatus 1 may be bent or deformed in response to a force applied by a user of the apparatus 1.

In some examples the first electrode 3 may also be transparent. The first electrode 3 may be optically transparent so that visible light can pass through the apparatus 1. This may make the apparatus 1 suitable for use in, for example, display devices.

The first electrode 3 may be made of any suitable electrically conductive material. For example, the first electrode may be made of gold, indium tin oxide (ITO), Fluorine doped tin oxide (FTO), Aluminium doped zinc oxide (AlZnO), poly (2,3-dihydrothieno-1,4-dioxin)-poly(styrenesulfonate) (PEDOT:PSS), polypyrrole (Ppy), Silver nanowires, carbon nanotubes and graphene based materials including composites thereof or any other suitable material.

The dielectric layer 7 may be provided overlaying the first electrode 3.

The dielectric layer 7 may be compressible. The dielectric layer 7 may be highly sensitive to being compressed so that the dielectric layer 7 can be used to detect small forces applied to the apparatus 1. This may enable the apparatus 1 to be used as a highly sensitive pressure sensor.

The dielectric layer 7 may be porous. In some examples the dielectric layer 7 may be highly porous. In some examples a substantial portion of the dielectric layer 7 may comprise void space. For example, about 40% of the dielectric layer 7 may comprise void space.

This porous nature of the dielectric layer 7 may make the dielectric layer 7 have a low resistance to being compressed and may make the apparatus 1 suitable for use a highly sensitive pressure sensor.

The dielectric layer 7 may be formed by self-assembly of block copolymers. In some examples the dielectric layer 7 may be formed by phase separation of block copolymers. The structure of dielectric layer 7 may be hierarchical. The hierarchical structure may comprise microstructural elements and nanostructural elements.

The microstructural elements may comprise the structure of the dielectric layer 7 which can be seen when the dielectric layer 7 is viewed under a microscope. The microstructural elements may have dimensions of the order of 10 s of micrometers.

The nanostructural elements may comprise structural elements of the dielectric layer 7 which are smaller than the microstructural elements. The nanostructural elements may comprise the arrangement of phases within the dielectric layer 7. The nanostructural elements may have dimensions of less than 100 nm. In some examples the nanostructural elements may have dimensions in a range of about 1 nm to about 100 nm.

The nanostructural elements may comprise the internal arrangement of the blocks of polymers, the pores and the boundaries between the phases or any other suitable elements.

Example methods of forming a suitable dielectric layer 7 are described below with reference to FIG. 2.

The dielectric layer 7 may be optically transparent so that visible light may pass through the dielectric layer 7. The dimensions of the nanostructural elements of the dielectric layer 7 may be such that the nanostructure does not cause scattering of light incident on the apparatus 1.

In the example of FIG. 1 the second electrode 5 is provided overlaying the dielectric layer 7. The second electrode 5 may comprise any suitable electrically conductive material provided overlaying the dielectric layer 7.

In some examples the second electrode 5 may also be flexible. The second electrode 5 may be flexible so that the apparatus 1 may be bent or deformed in response to a force applied by a user of the apparatus 1.

In some examples the second electrode 5 may also be transparent. The second electrode 5 may be optically transparent so that visible light can pass through the apparatus 1. This may make the whole of the apparatus 1 optically transparent and may make the apparatus 1 suitable for use in, for example, display devices.

The second electrode 5 may be made of any suitable electrically conductive material. For example, the second electrode 5 may be made of gold, indium tin oxide (ITO), Fluorine doped tin oxide (FTO), Aluminium doped zinc oxide (AlZnO), poly(2,3-dihydrothieno-1,4-dioxin)-poly(styrenesulfonate) (PEDOT:PSS), polypyrrole (Ppy), Silver nanowires, carbon nanotubes and graphene based materials including composites thereof or any other suitable material.

The first electrode 3 and the second electrode 5 may be arranged to form a parallel plate capacitor. The capacitance of the parallel plate capacitor may depend on the separation of the first electrode 3 and the second electrode 5 and the permittivity of the dielectric layer 7 between the two electrodes 3, 5.

When pressure is applied to the apparatus 1 this causes compression of the dielectric layer 7. This increases the capacitance of apparatus 1 because it decreases the thickness of the dielectric layer and so reduces the separation between the two electrodes 3, 5.

The compression of the dielectric layer 7 may also increase the permittivity of the dielectric layer 7. If the dielectric layer 7 is porous then, as the dielectric layer 7 is compressed, this causes air to be expelled from the dielectric layer 7. As air has a lower permittivity than the dielectric material which comprises the dielectric layer 7 this causes an increase in the permittivity of the dielectric layer 7. The resulting increase in the permittivity of the dielectric layer 7 causes an increase in the capacitance of the parallel plate capacitor formed by the first electrode 3 and the second electrode 5.

The apparatus 1 illustrated in FIG. 1 may be used as a sensor such as a pressure sensor. As the dielectric layer 7 is highly compressible it may be compressed when very small forces are applied to the apparatus 1. The compression of the dielectric layer 7 may be detected by detecting the resulting change in the capacitance of the parallel plate capacitor.

The parallel plate capacitor formed by the first and second electrodes 3, 5 may form part of a sensing circuit which may be configured to detect variations in the capacitance. In some examples a signal from the capacitor may be provided to a measurement device.

Figure 2:
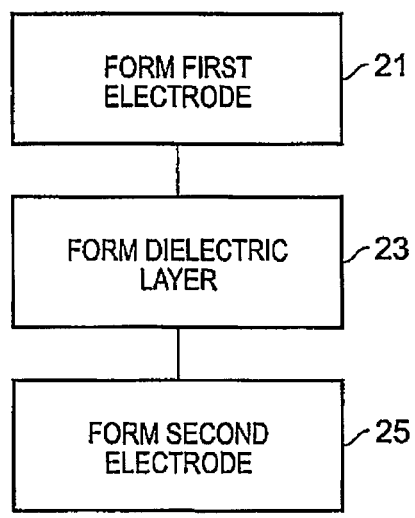
FIG. 2 illustrates a method according to an example of the disclosure.

FIG. 2 is a block diagram which schematically illustrates a method of forming an apparatus 1 such as the example apparatus 1 illustrated in FIG. 1.

At block 21 the first electrode 3 is formed. The first electrode 3 may be formed by evaporating 5 nm of chromium onto a PEN substrate followed by 100 nm of gold. The chromium may provide an adhesion layer for the gold. It is to be appreciated that in other examples other materials and/or thicknesses of the respective materials may be used.

It is also to be appreciated that different methods of forming the electrodes may be used. For example, if an optically transparent apparatus 1 is desired then the first electrode 3 may be formed by either sputtering of ITO, or transfer of chemical vapour deposition (CVD) graphene, or inkjet printing of graphene-based inks, or any other suitable method. In other examples the first electrode 3 may also be formed by electroplating, electroless plating, atomic layer deposition, chemical vapour deposition, electrochemical deposition, sputter coating or transfer of a graphene based material. The first electrode 3 may also be formed by solution coating of a conductive polymer such as PEDOT or Ppy or graphene based ink, this may be deposited by spin coating, meter-bar coating, rod coating, air-knife coating, slot-die coating, slide-hopper coating, curtain coating, screen printing, inkjet printing or any other suitable method.

The evaporation may be performed through a physical mask to enable the electrodes 3 to be formed in a particular size or shape. In an example the mask may allow the creation of stripes of the conductive material along the substrate. The stripes may be around 10 mm wide.

At block 23 the dielectric layer 7 is formed. The dielectric layer 7 may be formed from a block copolymer. In an example the block copolymer may comprise polystyrene (PS) and polylactic acid (PLA). In a particular example the molecular weight may be Mw=23.8 kg mol$^{-1}$ and the polydispersity index may be $M_w/M_n$=1.10. In the particular example the block copolymer is dissolved in toluene to form a solution with a concentration of about 11% w/w. It is to be appreciated that other polymers may be used in other examples and that other molecular weights and concentrations of solutions may be used in other examples.

The block polymer solution is then coated overlaying the first electrode 3. The block copolymer solution may be coated over the electrode using any suitable technique which may enable a uniform layer to be created. In some examples the block copolymer solution may be spin coated or blade coated over the first electrode 3. The thickness of the layer of the block copolymer solution may be between 0.5 to 20 micrometers. It is to be appreciated that any suitable thickness of the block copolymer solution may be used in various examples.

The block copolymer solution may then be annealed. The block copolymer solution may be annealed in a vacuum and inert atmosphere. In the particular example the block copolymer solution may be annealed at a temperature of 173 degrees Celsius for about 20 minutes.

After the block copolymer solution has been annealed it is cooled to about room temperature. The PLA phase is then removed by etching. The PLA phase may be chemically removed by soaking the apparatus 1 in a solution. For example the apparatus 1 may be soaked in a 0.1M NaOH in 50:50 water:methanol solution for about three hours. It is to be appreciated that other solutions or methods may be used in other examples for instance in some cases UV light can be used to remove one of the phases.

Once the PLA phase has been removed this may leave void spaces between the PS phase to create a porous structure. The amount of void space may depend on the ratios of the respective components of the block copolymer.

The nanostructure of the dielectric layer 7 which is obtained may depend on a plurality of factors which may include the polymers that are used to form the block copolymer and also the ratios of the respective polymers. For example using different rations of two polymer blocks may change the resulting phase separated structure. A ratio of 50:50 may result in a lamellar structure. The thickness of the lamellae may be determined by the length of the polymer chains in each block. A ratio of 60:40 may result in dispersion of the minority phase in the form of cylinders within the majority phase to give a cylindrical phase.

In the example apparatus 1 described above PS and PLA are used as the blocks of the copolymer. It is to be appreciated that any suitable polymers may be used in other examples. For example, the block copolymer may comprise any two or more chemically distinct polymers such as polystyrene, polylactide, polymethylmethacryclate (PMMA), polyimide, polyfluorostyrene, polybutadiene, polyisoprene, polydimethylsiloxane (PDMS), polyvinylpyridine (PVP) or any suitable polymer. The block copolymer may comprise two or more chemically distinct polymers linked together by a covalent bond at one end of polymer. The block copolymer may have the ability to self assemble into a variety of different phase morphologies such as spherical, vertically oriented pillar, horizontally-oriented pillar, gyroid, double gyroid, vertically-oriented lamellar and horizontally-oriented lamellar structures. The structures which are formed may depend on factors such as the volume fraction and molecular weight of the component polymers.

The second electrode is then adhered to the dielectric layer 7. The second electrode 5 may be adhered in direct contact with the dielectric layer 7.

It is to be appreciated that other methods of manufacturing the apparatus 1 may be used in other examples.

Figure 3:
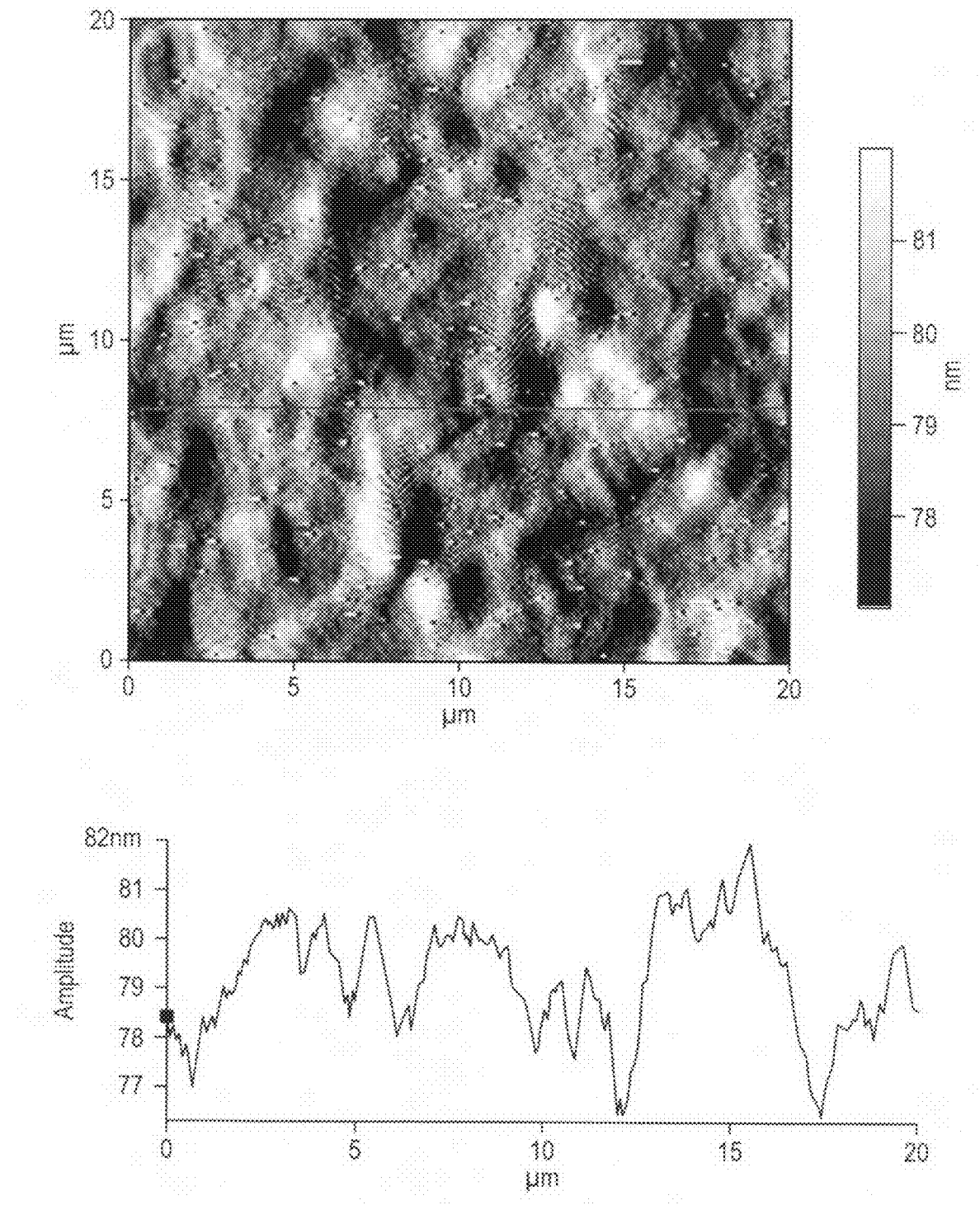
FIG. 3 illustrates the microstructure of an example dielectric layer.

The dielectric layer 7 which is formed using the methods described above maybe hierarchical so it may comprise both microstructural elements and nanostructural elements. FIG. 3 illustrates the microstructure of an example dielectric layer 7 formed using a method such as the method described above.

FIG. 3 shows an image of an example dielectric layer 7 obtained using an atomic force microscope. The images in FIG. 3 show a roughness variation in the order of 5 to 10 micrometers.

Figure 4:
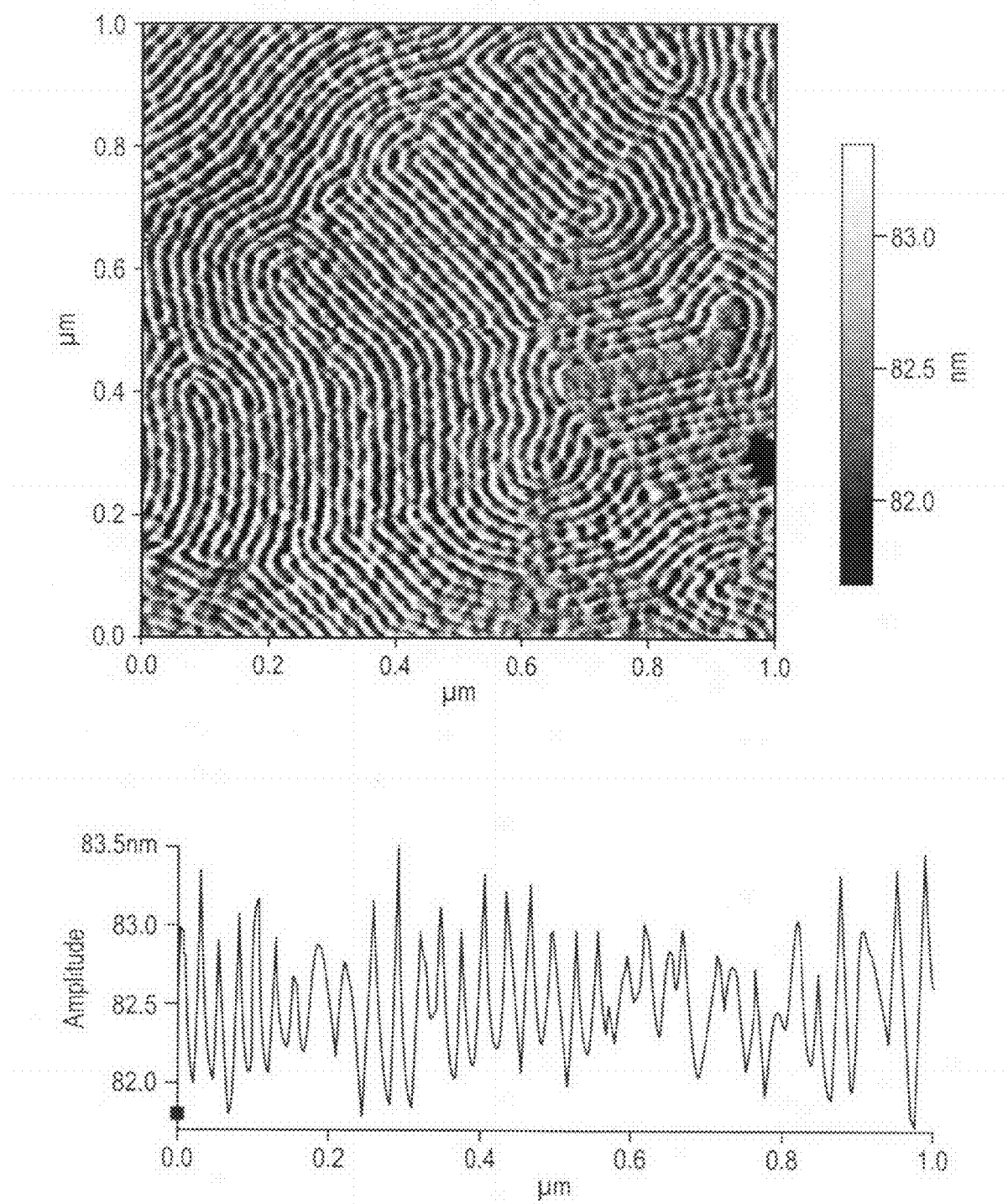
FIG. 4 illustrates the nanostructure of an example dielectric layer.

FIG. 4 illustrates the nanostructure of an example dielectric layer 7 formed using the method described above.

FIG. 4 shows an image of an example dielectric layer 7 obtained using higher resolution microscope. The images in FIG. 4 show a roughness variation in the order of 25 to 100 nanometers. The nanostructure of the dielectric layer comprises the horizontal cylindrical phase of the polystyrene polymer.

Figure 5:
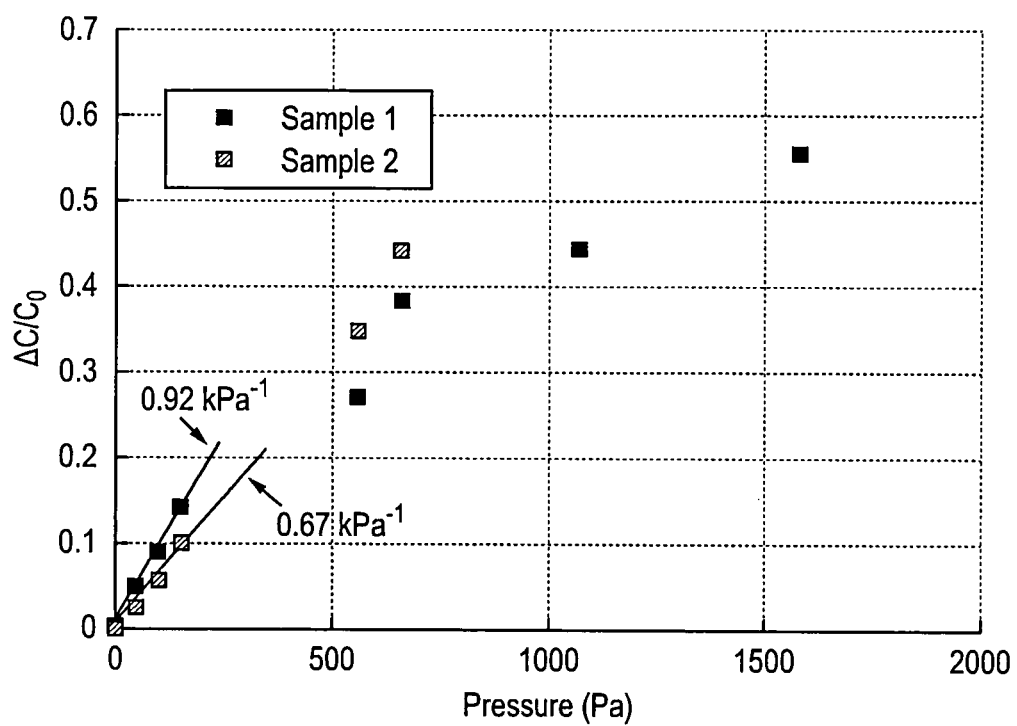
FIG. 5 illustrates measurements obtained using an example apparatus.

FIG. 5 illustrates results obtained using a test apparatus 1 as described above. In the test apparatus the area of the parallel plate capacitor was about 25 mm$^2$.

To obtain the test results the apparatus 1 was placed on a rigid surface and electrical contact was made to each of the electrodes 3, 5. The capacitance was measured using an LCR meter. Weights were added to the top surface of the apparatus 1 and the change in the capacitance was measured. The contact area between the weight and the apparatus 1 was kept constant.

FIG. 5 illustrates the capacitance response for two different sample apparatus 1 as a function of pressure. It can be seen from the plot that the apparatus 1 is very sensitive to low pressures at that at higher pressures the response begins to saturate.

The apparatus 1 illustrated in FIG. 1 and described above may be configured to be worn on the body of the user of the apparatus 1. This may enable the apparatus 1 to be used to detect physiological conditions of the user. For example the apparatus 1 may be attached to an adhesive portion or tape which may be attached to the skin of the user or the apparatus 1. In other examples the apparatus 1 may be attached to a strap which may be attached to the body of a user.

Figure 6:
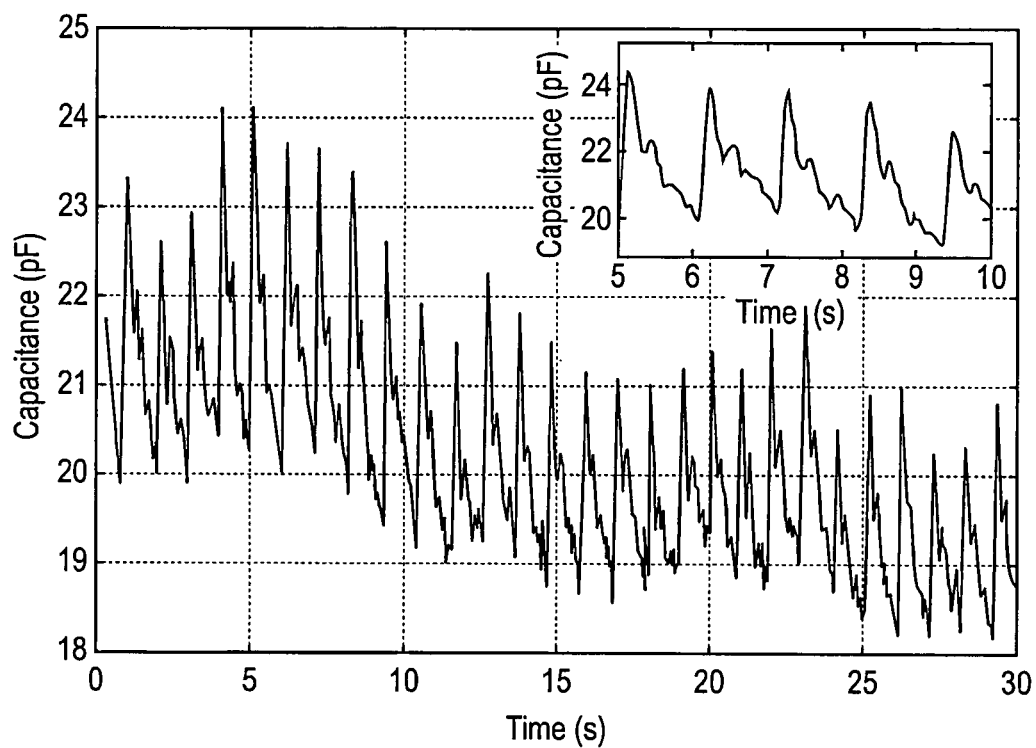
FIG. 6 illustrates measurements obtained using an example apparatus attached to a user.

FIG. 6 illustrates test results which were obtained when a test apparatus 1 as described above was attached to the wrist of a user.

The apparatus 1 is attached to the body of the user so that the pulse of user applies a pressure to the apparatus. To obtain the results illustrated in FIG. 6 the apparatus 1 was attached to the wrist of the user using an adhesive tape.

Once the apparatus 1 is attached to the user, the pulse causes compression of the dielectric layer 7. As mentioned above, the compression of the dielectric layer 7 increases the capacitance of the parallel plate capacitor. In the example of FIG. 6 the capacitance was measured as a function of time using an LCR meter to enable the user's heartbeat to be monitored.

The results obtained show the periodic systolic pressure fluctuation due to the heart beats of the user. The insert in FIG. 6 shows an increased scale of the results and indicates that the apparatus 1 is detected the decrease in pressure as the aortic valve closes and the diastolic phase of the cardiac cycle begins.

Figure 7:
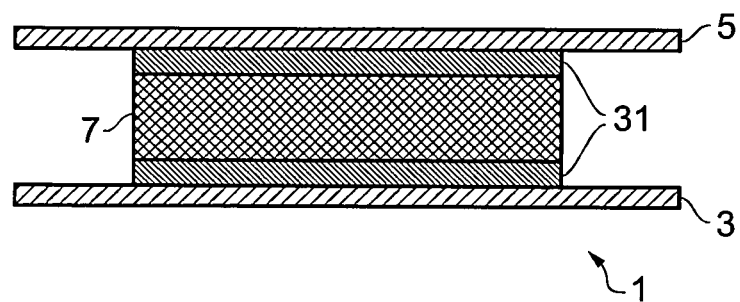
FIG. 7 illustrates an apparatus according to another example of the disclosure.

FIG. 7 illustrates an apparatus 1 according to another example of the disclosure. The example apparatus 1 of FIG. 7 comprises a first electrode 3, a second electrode 5 and a dielectric layer 7 which may be as described above in relation to FIG. 1. The apparatus 1 of FIG. 7 may be formed using methods as described above in relation to FIGS. 2 to 4

The apparatus 1 illustrated in FIG. 7 differs from the apparatus 1 illustrated in FIG. 1 in that it comprises additional dielectric layers 31. In the particular example of FIG. 7 two additional dielectric layers 31 are provided. The additional dielectric layers 31 are provided between the electrodes 3, 5 and the nanostructured dielectric layer 7. It is to be appreciated that in other examples only one dielectric additional dielectric layer 31 might be provided.

The additional dielectric layers 31 may be arranged to avoid short circuit of the two electrodes 3, 5 when subjected to high pressure. The additional dielectric layers 31 may be transparent, continuous, and non-porous. The additional dielectric layers 31 may be made of any suitable material.

The first additional dielectric layer 31 may be deposited on the first electrode 3 prior to creation of the nano-structured porous dielectric layer 7. The second additional dielectric layer 31 may be deposited on the nano-structured porous dielectric layer 7 so that the second electrode 5 is provided overlaying the second additional dielectric layer 31.

The examples described above relate to an apparatus 1 which may be used as high sensitivity pressure sensor. The pressure sensor may be used a wide range of applications. For instance, in some examples the pressure sensor may be used to detect a user input which may enable a user to control a device by making selections or changing settings. In other examples the apparatus may be used to monitor the heart rate of the user or other suitable physiological conditions.

In the above mentioned examples the dielectric layer 7 is formed by self-assembly. In the particular example the dielectric layer 7 is formed by phase separation. This may provide a simple method of manufacturing nanostructured material which may be used to make a large number of devices. As there is no replication step or need for the use of a mold to form the nanostructure this makes the dielectric layer 7 less susceptible to defects.

In some examples the apparatus 1 may be fully transparent. For example, the dielectric layer 7 and the electrodes 3, 5 and the substrate 9 may all be permeable to visible light. In such examples the apparatus 1 may be combined with a display of other graphic motifs. This may enable the apparatus 1 to be used in a wide range of applications.

In some examples a plurality of apparatus 1 as described above may be provided in an array. In such examples each of the apparatus 1 in the array may be arranged to provide an output independently of the other apparatus 1 in the array.

Having an array of apparatus 1 rather than a single apparatus 1 may increase the reliability of sensors formed from the apparatus 1 as it may allow for averaging of multiple results. The array of apparatus 1 may also provide improved signal to noise ratios and improve the positional tolerance of the apparatus.

The blocks illustrated in the FIG. 2 may represent steps in a method and/or sections of code in a computer program. The illustration of a particular order to the blocks does not necessarily imply that there is a required or preferred order for the blocks and the order and arrangement of the block may be varied. Furthermore, it may be possible for some blocks to be omitted. It is to be appreciated that in some examples additional blocks may be included.

The term 'comprise' is used in this document with an inclusive not an exclusive meaning. That is any reference to X comprising Y indicates that X may comprise only one Y or may comprise more than one Y. If it is intended to use 'comprise' with an exclusive meaning then it will be made clear in the context by referring to "comprising only one." or by using "consisting".

In this brief description, reference has been made to various examples. The description of features or functions in relation to an example indicates that those features or functions are present in that example. The use of the term 'example' or 'for example' or 'may' in the text denotes, whether explicitly stated or not, that such features or functions are present in at least the described example, whether described as an example or not, and that they can be, but are not necessarily, present in some of or all other examples. Thus 'example', 'for example' or 'may' refers to a particular instance in a class of examples. A property of the instance can be a property of only that instance or a property of the class or a property of a sub-class of the class that includes some but not all of the instances in the class.

Although embodiments of the present invention have been described in the preceding paragraphs with reference to various examples, it should be appreciated that modifications to the examples given can be made without departing from the scope of the invention as claimed.

In some examples the capacitive sensor may be constructed such that one of the electrodes forms the channel of a metal oxide semiconductor field effect transistor (MOSFET) and the other electrode is the gate such that a modulation of the capacitance results in a change in the drain-source current of the MOSFET. An example may be a graphene transistor.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

We claim:

1. An apparatus comprising:
a first electrode and a second electrode arranged to form a parallel plate capacitor;
a compressible, transparent dielectric layer provided between the first electrode and the second electrode wherein the dielectric layer has both a nanostructure and a microstructure, and the dimensions of the nanostructure are such that the dielectric layer is optically transparent;
wherein the dielectric layer is porous;
wherein the dielectric layer is formed from a block copolymer; and
wherein the nanostructure and the microstructure of the dielectric layer define a hierarchical structure.

2. An apparatus as claimed in claim 1 wherein the nanostructure of the dielectric layer is formed by self assembly of the block copolymer.

3. An apparatus as claimed in claim 1 wherein the nanostructure of the dielectric layer is formed by phase separation of the block copolymer.

4. An apparatus as claimed in claim 2 wherein the dimensions of the nanostructure are such that the nanostructure does not cause scattering of incident light.

5. An apparatus as claimed in claim 1 wherein the dimensions of the nanostructure are less than 100 nm.

6. An apparatus as claimed in claim 1 wherein the first electrode is formed on a curved surface.

7. An apparatus as claimed in claim 1 wherein the electrodes are at least one of transparent and flexible.

8. An apparatus as claimed in claim 1 wherein the signal from the capacitor is configured to be provided to measurement apparatus.

9. An apparatus as claimed in claim 1 wherein the apparatus is configured to be worn on a body of a user.

10. An array comprising a plurality of apparatus as claimed in claim 1.

11. An apparatus as claimed in claim 1, wherein the microstructure of the dielectric layer comprises elements having dimensions of the order of tens of micrometers.

12. An apparatus as claimed in claim 1, wherein the nanostructure of the dielectric layer comprises elements having dimensions in a range of about 1 nm to about 100 nm, and wherein the microstructure of the dielectric layer comprises elements having dimensions of the order of tens of micrometers.

13. An apparatus as claimed in claim 1, wherein the nanostructure of the dielectric layer comprises elements comprising an internal arrangement of one or more of blocks of the block copolymer, pores, and boundaries between phases of block copolymer.

14. An apparatus as claimed in claim 1, wherein at least the first electrode comprises a polymer substrate, an adhesion layer of chromium on the polymer substrate, and a layer of gold on the adhesion layer.

15. An apparatus as claimed in claim 14, wherein the polymer substrate comprises polyethylene 2,6-naphthalate (PEN), polyethylene terephthalate (PET), polyimide (PI), polycarbonate (PC), polyethylene (PE), polyurethane (PU), polymethylmethacryclate (PMMA), or polystyrene (PS).

16. An apparatus as claimed in claim 1, wherein the block copolymer comprises polystyrene and polylactic acid.

17. An apparatus, comprising:
a first electrode and a second electrode arranged to form a parallel plate capacitor; and
a compressible, transparent, and porous dielectric layer formed from a block copolymer provided between the first electrode and the second electrode wherein the dielectric layer has both a nanostructure and a microstructure, and the dimensions of the nanostructure are such that the dielectric layer is optically transparent;
wherein the first electrode comprises a polymer substrate of polyethylene 2,6-naphthalate (PEN), an adhesion layer of chromium on the polymer substrate, and a layer of gold on the adhesion layer; and
wherein the block copolymer comprises polystyrene and polylactic acid.

18. An apparatus comprising:
a first electrode and a second electrode arranged to form a parallel plate capacitor;
a compressible, transparent dielectric layer provided between the first electrode and the second electrode wherein the dielectric layer has both a nanostructure and a microstructure, and the dimensions of the nanostructure are such that the dielectric layer is optically transparent;
wherein the dielectric layer is porous;
wherein the dielectric layer is formed from a block copolymer; and
wherein the nanostructure of the dielectric layer comprises elements comprising an internal arrangement of one or more of blocks of the block copolymer, pores, and boundaries between phases of block copolymer.

19. An apparatus as claimed in claim 18 wherein the first electrode is formed on a curved surface.

20. An apparatus as claimed in claim 18 wherein the electrodes are at least one of transparent and flexible.

* * * * *